United States Patent [19]

Putzig et al.

[11] Patent Number: 4,953,621

[45] Date of Patent: * Sep. 4, 1990

[54] ORGANIC TITANIUM COMPOSITIONS USEFUL AS CROSS-LINKERS

[75] Inventors: Donald E. Putzig, Newark; Kenneth C. Smeltz, Wilmington, both of Del.

[73] Assignee: E. I. Du Pont de Nemours and Company, Wilmington, Del.

[*] Notice: The portion of the term of this patent subsequent to Sep. 2, 2003 has been disclaimed.

[21] Appl. No.: 349,881

[22] Filed: May 9, 1989

Related U.S. Application Data

[63] Continuation of Ser. No. 77,020, Jul. 23, 1987, abandoned, which is a continuation of Ser. No. 714,513, Mar. 21, 1985, abandoned.

[51] Int. Cl.$^5$ .................... E21B 43/26; E21B 43/267
[52] U.S. Cl. ................................ 166/308; 252/8.551; 252/315.3
[58] Field of Search ............... 252/8.551, 8.553, 315.3; 166/308

[56] References Cited

U.S. PATENT DOCUMENTS

| | | | |
|---|---|---|---|
| 2,680,108 | 6/1954 | Schmidt | 260/429.5 |
| 2,870,181 | 1/1959 | Shacklett | 260/429.5 |
| 2,898,356 | 8/1959 | Russell | 260/429.5 |
| 2,950,174 | 8/1960 | Lagally | 23/202 |
| 3,301,723 | 1/1967 | Chrisp | 149/20 |
| 3,888,312 | 6/1975 | Tiner et al. | 166/308 |
| 4,462,917 | 7/1984 | Conway | 252/8.55 R |
| 4,464,270 | 8/1984 | Hollenbeak et al. | 252/8.55 R |
| 4,609,479 | 9/1986 | Smeltz | 252/8.551 |

OTHER PUBLICATIONS

Rummo: Crosslinking Delay Achieved with Gel Additive, Oil & Gas Journal, Sep. 13, 1982 Technology, pp. 84 & 89.

Primary Examiner—George A. Suchfield

[57] ABSTRACT

Novel aqueous titanium compositions comprising mixtures of at least two titanium compounds, at least one of which effects cross-linking of hydroxyl-containing materials more rapidly than at least one other titanium compound; the use of such organic titanium compositions in a novel process for hydraulically fracturing oil- and/or gas-containing subterranean formations; and aqueous compositions useful in such a process.

28 Claims, No Drawings

ORGANIC TITANIUM COMPOSITIONS USEFUL AS CROSS-LINKERS

This application is a continuation-in-part of application Ser. No. 07/077,020 filed July 23, 1987, now abandoned, which is a continuation of Ser. No. 714,513 filed Mar. 21, 1985, now abandoned.

SUMMARY OF THE INVENTION

The present invention relates to novel aqueous titanium compositions comprising mixtures of at least two titanium compounds, at least one of which effects cross-linking of hydroxyl-containing materials more rapidly than at least one other titanium compound. It relates also to the use of such organic titanium compositions in a novel process for hydraulically fracturing oil- and/or gas-containing subterranean formations. It relates in addition to aqueous compositions useful in such a process.

BACKGROUND OF THE INVENTION

Titanium esters react with high molecular weight hydroxyl-containing compounds so as to cross-link them and produce gels, J. Oil and Colour Chem. Assoc. 31, 405 (1948). As the cross-linking rate of simple alkyl esters of titanium is too fast for some industrial uses, it has been depressed by combining titanium esters with a variety of multifunctional compounds; e.g., the complex condensation products prepared by Shacklett, U.S. Pat. No. 2,870,181, by reacting an organotitanate with an α-hydroxy carboxylic acid such as lactic acid; the organic titanate chelates obtained by reacting alkyl titanates with 2,4-pentanedione or an acetoacetate, U.S. Pat. No. 2,680,108; also those prepared by reacting alkyl titanates with alkanolamines, U.S. Pat. Nos. 2,950,174 and 3,301,723.

The production of oil and gas can be stimulated by a technique, known as hydraulic fracturing, in which a fluid composition is introduced into an oil- or gas-containing subterranean formation at a flow rate and pressure which create and/or extend a fracture into the formation. The fluid composition usually carries a proppant (e.g., sand, bauxite, etc.) which is forced into the fracture by the fluid composition and prevents closure of the fracture after the fluid pressure is released. For example, Tiner, et al., U.S. Pat. No. 3,888,312, disclose effecting hydraulic fracturing of a subterranean formation by using an aqueous gel prepared from a solvatable polysaccharide which had been cross-linked with an organotitanate chelate prepared by reacting tetraisopropyl titanate with triethanolamine. The rate at which such aqueous gels are cross-linked by such an organotitanate chelate can be retarded further by adding a polyol to the aqueous gel prior to admixing it with such an organotitanate chelate, Hollenbeak et al., U.S. Pat. No. 4,464,270. On the other hand, Conway, U.S. Pat. No. 4,462,917, retarded the cross-linking rate of that same organotitanate chelate by admixing it with a polyol and aging the admixture for 3 to 12 weeks prior to combining the same with the aqueous gel.

The fluid composition used in hydraulic fracturing comprises an aqueous fluid (usually water or aqueous alcohol), a polymeric gelling agent (e.g., a solvatable polysaccharide), and a cross-linking agent. The aqueous fluid is used to solvate the gelling agent, and the solvated gelling agent, which is to be cross-linked, is typically referred to as the "base gel." The pH of the base gel can be adjusted with various buffering agents prior to cross-linking. The rate of cross-linking determines the rate of viscosity development in the fluid composition. It is desirable to control the rate of cross-linking so that the development of viscosity is delayed until the composition is placed in the subterranean formation.

Several factors influence rate of cross-linking. It is directly proportional to the concentration of the polymeric gelling agent and the temperature of the base gel, so that an increase in the gelling agent concentration or the gel temperature causes an increase in the rate of cross-linking. On the other hand, as the temperature of the subterranean formation is cooled by injection of the fluid composition, the rate of cross-linking decreases. The pH of the base gel has its effect on cross-linking as well; as the pH of the base gel increases from 7.0 to 8.5, the rate of cross-linking increases. Because more than one batch of base gel is used in any fracturing job, and because conditions such as base gel temperature and formation temperature vary from job to job and with the time of year, it is desirable to use a cross-linking agent or agents which have a variable or adjustable rate of cross-linking to compensate for these changes and provide a reproducible viscosity development time after time.

Cross-linking agents having a high rate of cross-linking may give a cross-linked gel (e.g., from hydroxypropyl guar) which exhibits poor retention of viscosity with time, also with increased temperature. Moreover, use of such high rate cross-linkers may give gels which develop high viscosity while the gel is being pumped down to the subterranean formation, resulting in shear degradation which reduces or destroys the capacity of the base gel to maintain the proppant (e.g., sand) in suspension. As a consequence, the proppant may drop out of suspension (a "screen-out") and may block the bottom of the well tubing. Excessively high viscosities are not encountered in pumping gels cross-linked with low rate cross-linkers, and therefore such cross-linkers avoid shear degradation. But one may none-the-less experience screen-outs with the use of low rate cross-linkers because the gel fails ever to reach a viscosity high enough to keep the proppant in suspension while being pumped down into the formation.

DETAILED DESCRIPTION OF THE INVENTION

The novel composition and process of this invention overcome the disadvantages associated with those of the prior art. The compositions are such that development of the high viscosity needed for hydraulic fracturing takes place as the aqueous gel reaches the formation to be fractured, thus avoiding excessive shear degradation. The process of this invention enables one to accommodate changes in temperature, pH and polymeric gel concentration as they are encountered in the field.

In the compositions of the present invention, one uses at least two aqueous titanates prepared by reacting a tetravalent titanium compound of an inorganic acid with an α-hydroxycarboxylic acid, a polyol and water. In such a composition, at least one of the aqueous titanates effects cross-linking of hydroxyl-containing compounds (e.g., a solvatable polysaccharide) more rapidly than at least one other aqueous titanate contained in the compositions.

The α-hydroxy carboxylic acids useful according to the invention may be monocarboxylic acids, such as lactic acid and glycolic acid; dicarboxylic acids, such as malic acid; or tricarboxylic acids, such as citric acid. Moreover, they can be polyhydroxypolycarboxylic acids such as tartaric acid or saccharic acid, monocarboxylic acids having a plurality of hydroxy groups, such as gluconic acid and gylceric acid, or aromatic hydroxy acids such as mandelic acid. The polyols also vary widely. In general, they are trihydric, tetrahydric, pentahydric or hexahydric alcohols, including glycerol, erythritol, arabitol, xylitol, sorbitol, dulcitol, mannitol, and inositol. Other polyols useful in the invention include monosaccharides, e.g., glucose, fructose, mannose, galactose and xylose, as well as disaccharides such as sucrose, lactose, maltose and cellobiose. Sorbitol is the preferred polyol for purposes of the invention.

The aqueous titanates useful according to this invention can be prepared by either of the methods disclosed by Smeltz in U.S. Pat. No. 4,609,479 and U.S. Patent Application Ser. No. 678,016 filed Dec. 4, 1984, now abandoned, the contents of both of which are incorporated herein by reference. In the former, one combines a polyol, water and an α-hydroxy carboxylic acid, and then reacts that combination of materials with a tetravalent titanium compound of an inorganic acid. In the latter, one forms an aqueous solution of an α-hydroxy carboxylic acid, reacts said aqueous solution with a tetravalent titanium compound of an inorganic acid, and reacts the resulting material with a polyol. In a preferred embodiment of each method, the so-formed composition is neutralized with a suitable base. Likewise, in each, the starting materials may be present at mol ratios in the range between about 1 to 3 mols of hydroxy acid per mol of titanium and between about 0.25 to 2 mol of polyol per mol of titanium. Preferably, the water content of the compositions is in the range between 36 and 60 mols of water per mol of titanium. In most cases neutralization of the composition is effected to a pH in the range between 6.5 and 9.

In accordance with the hydraulic fracturing process of the present invention, one can establish and maintain a desired cross-linking rate by using a mixture of cross-linkers which cross-link at two different rates, i.e., fast and slow, fast and moderate, or moderate and slow. In the colder winter months, or as injection of the fluid composition cools the formation, or as pH becomes more acidic, more of the faster cross-linking component is used. In the summer months or as the temperature of the formation increases or pH is raised or with an increase in the depth at which the formation is located, more of a slower cross-linker is used. In this way, the rate of cross-linking and viscosity development can be controlled in a reproducible fashion between the extremes of the components of the mixture.

The proportions of the different aqueous titanates in the composition used in the process of this invention can be determined empirically as a function of gel temperature, subterranean formation depth, subterranean formation temperature, pH of the base gel and of the formation, and base gel concentration. As any of those parameters changes, the proportion of the slower or faster cross-linker can be changed accordingly. Thus, for example, one would commence a hydraulic fracturing operation with at least two aqueous titanates at a ratio which is suitable for base gel pH and temperature as well as the depth and temperature of the formation. As the fluid composition is pumped into the subterranean formation, the temperature of the formation will decrease. At that point, the proportion of the faster cross-linker in the composition of this invention is increased. For example, one can vary the volume:volume ratio of a faster cross-linker to a slower cross-linker in range of about 10:1 to about 1:10, usually about 3:1 to 1:3. In a preferred embodiment, 1 volume of the aqueous reaction product of 1 mol of TiCl$_4$ plus 1 mol of lactic acid plus ½ mol of sorbitol is combined with 1 volume of the aqueous reaction product of 1 mol of TiCl$_4$ plus 1 mol of malic acid plus 1 mol of sorbitol.

The solvatable polysaccharides useful in the process of the invention include guar gum and locust bean gum, as well as other galactomannan and glucomannan gums, such as those derived from sennas, Brazilwood, Tera, Honey locust, Karaya gum and the like. Derivatives of such gums are useful also, e.g., hydroxyethylguar, hydroxypropylguar, carboxyethylhydroxyethylguar, carboxymethylhydroxypropylguar, and the like, as well as cellulose derivatives containing carboxyl groups, such as carboxymethylcellulose, carboxymethylhydroxyethylcellulose, and the like. Hydroxypropylguar and carboxymethylhydroxypropylguar are preferred polysaccharides for use in the present invention. Hydroxypropylguar is the most preferred gum based upon its commercial availability and desirable properties. On the other hand, carboxymethylhydroxypropylguar is sometimes used in place of hydroxypropylguar in fracturing fluids when the permeability of the formation is such that one wishes to keep the residual solids at a low level, so as to prevent formation damage. The solvatable polysaccharides can be used individually or in combination; usually, however, a single material is used. The solvatable polysaccharides are normally blended with a solvent such as water or an aqueous medium (e.g., aqueous methanol, ethanol, 1 to 3% HCl or potassium chloride) to form an uncrosslinked gel as a first step.

The amounts of solvatable polysaccharide and the cross-linker composition therefor vary. One uses small but effective amounts which for both will vary with the circumstances, e.g., the type of geologic formation, the depth at which fluid fracturing is to be performed, temperature, pH, etc. Moreover, the type of cross-linker composition that is chosen will vary also with some of the same factors. In addition, the rates of cross-linking will be a factor to be considered in choosing the mixture of titanium compounds. The aqueous titanium compounds of lactic and glycolic acids give approximately the same rate of cross-linking, with others in the following descending order: glycolic and lactic acids > malic acid > tartaric acid > citric acid > gluconic acid. In all cases, one uses as small an amount of each in water as will provide the viscosity level necessary to effect fracturing of the subterranean formation to the extent necessary to promote adequate recovery of oil or gas from it. For example, satisfactory gels can generally be made by using the solvatable polysaccharide in amounts up to about 1.5 weight percent and up to about 0.35 weight percent of the cross-linker composition, both percentages being based on the weight of the aqueous liquid. Preferably, from about 0.3 to about 0.7 weight percent of the solvatable polysaccharide is used and from about 0.075 to about 0.15 weight percent of the cross-linker composition.

The following Examples are given in further illustration of the invention but not by way of limitation. The mixtures of aqueous titanates are described in the Table in terms of the volume ratio (v/v) of one titanate to another. So as to illustrate their suitability for use in hydraulic fracturing processes, the mixtures of aqueous titanates set forth in the Examples were used in two types of tests. One of the tests measures the viscosity imparted to hydroxypropylguar as a result of having been cross-linked by the mixtures of aqueous titanates, and the other measures the rate at which such mixtures of aqueous titanates effect cross-linking of hydroxypropylguar. For a pH 7 base gel, one blends for 30 minutes in a Waring Blender at a pH of 7: a fumaric acid/sodium bicarbonate buffer, 4.5 g of hydroxypropylguar and 0.9 g of sodium thiosulfate in 750 ml of 2% by weight KCl. If one wants a pH 8.6 gel, the fumaric acid is omitted. Unless specified otherwise, a pH 8.6 gel is used in the Examples.

The method for taking viscosity measurements involves the use of the FANN 50 Viscometer. To the foregoing quantity of base gel in a 1500 ml beaker one adds 0.75 ml of cross-linker solution containing 0.00064 mol of titanium. A 25 ml sample of that cross-linker-containing gel is placed in the cup of the FANN 50 Viscometer with an R-1, B-3 configuration at 250° F. (121° C.) and 100 rpm (88 sec$^{-1}$) shear. The rate of cross-linking is determined by measuring the period of time required to achieve maximum viscosity in the FANN 50 Viscometer procedure described above.

PREPARATION OF RAW MATERIALS

The procedures described below and the compositions thereby prepared are typical of those that were used for preparing the compositions used in the Examples that follow. Each of the procedures was carried out in a closed vessel containing an agitator, thermometer, condenser, nitrogen inlet and dropping funnel. Unless specified otherwise, percentages are given by weight and temperatures are given in degrees Celsius.

A. $TiCl_4$ + Lactic Acid + Sorbitol

1. Sorbitol (464.1 g) and lactic acid (516.9 g of an 88.8% aqueous solution) were dissolved in deionized water (1836 g) and swept slowly with nitrogen. Titanium tetrachloride (969 g) was added dropwise over a 1 hour and 44 minute period at a pot temperature of 23–25.5°. After 49 minutes of additional stirring at 25°, aqueous sodium hydroxide (2954.5 g of a 33% solution) was added dropwise over a 2 hour and 12 minute period at 23–27° to a pH of 7.2. A portion of the product (89.9 g) was used for storage testing. The remaining portion of the product was heated to 60° over a ten minute period and maintained at that temperature for two hours. It was cooled to about 25°, and aqueous sodium hydroxide (50.8 g of a 33% solution) was added to a pH of 7.2. The aqueous product, a solution having a total weight 6769 g (including the 89.9 g test sample), contained 3.63% titanium, with a Ti:lactic acid:sorbitol mol ratio of 1:1:0.5.

2. The corresponding aqueous product having a Ti:lactic acid:sorbitol mol ratio of 1:1:1 was prepared by essentially the same procedure (910 g of sorbitol, 511 g of 88% aqueous lactic acid, 1746 g of deionized water, 950 g of $TiCl_4$, and 3013.8 g of 33.0% aqueous NaOH).

B. $TiCl_4$ + Malic Acid + Sorbitol

1. Sorbitol (436.8 kg) and d,l-malic acid (224.5 kg) were dissolved in water (226.8 kg) and swept slowly with nitrogen. At 25–35°, $TiCl_4$ (324.8 kg) was added dropwise over a period of about 3.5 hours and stirring was continued at 30±5° for an additional 30 minutes. Aqueous NaOH (1408 kg of a 30% solution) was added dropwise at 30±5° over a period of about 4.5 hours resulting in a pH of 8.1. The product was heated to 80±2° over a period of about 45 minutes, maintained at that temperature for four hours, and cooled to about 25° over a period of about 45 minutes to give a product, an aqueous solution, having a pH of 7.2. Water (83.9 kg) was added, giving an aqueous solution which contained 2.93% by weight titanium.

2. A second charge was prepared based upon 435.9 kg of sorbitol, 224.5 kg of d,l-malic acid, 222.7 kg of water, 324.3 kg of $TiCl_4$ and 1300 kg of a 30% aqueous solution of sodium hydroxide. The procedure utilized was essentially that described above. The product, an aqueous solution weighing 2525.6 kg, was combined with 118.8 kg of the product of the first charge described above. The product had a titanium content of 3.11% by weight and a Ti:malic acid:sorbitol mol ratio of 1:1:1.

C. $TiCl_4$ + Citric Acid + Sorbitol

Citric acid monohydrate (945 g) and sorbitol (819 g) were dissolved in deionized water (1620 g) and swept slowly with nitrogen. At 22–24°, $TiCl_4$ (855 g) was added dropwise over a two hour and eight minute period, and stirring was continued at 25° for an additional 32 minutes. Aqueous NaOH (4033 g of a 30.3% solution) was added dropwise at 21–28° over a period of about five hours resulting in a pH of 7.5. The product was an aqueous solution which weighed 8240 g and contained 2.62% by weight of titanium. A portion of the product (78.2 g) was withdrawn for density measurement. The remainder of the product was heated to 60±2° over a 35 minute period and maintained at that temperature for two hours. It was cooled to about 25°, giving a pH of 7.1. The aqueous product had a Ti:citric acid:sorbitol mol ratio of 1:1:1.

TABLE

| Example | Gel pH | Mixture of Titanate Solutions (v:v) | Jabsco Pump Time (seconds) | Rate of Cross-Linking (minutes) | FANN Viscosity (centipoises) | | | | |
|---|---|---|---|---|---|---|---|---|---|
| | | | | | 0 Min. | 30 Min. | 60 Min. | 90 Min. | Maximum |
| 1 | 7.0 | A.1. + B.2.(3:1) | 15 | 2.5 | 168 | 290 | 250 | 220 | 450 |
| 2 | 7.0 | A.1. + B.2.(2:1) | 15 | 3.0 | 163 | 245 | 220 | 200 | 360 |
| 3 | 7.0 | A.1. + B.2.(1:1) | 15 | 4.0 | 125 | 227 | 200 | 180 | 305 |
| 4 | 7.0 | A.1. + B.2.(1:2) | 15 | 6.5 | 105 | 218 | 195 | 172 | 282 |
| Control A.1. | 7.0 | — | 15 | 1.5 | 325 | 350 | 317 | 290 | 600 |
| Control B.2. | 7.0 | — | 15 | 7.0 | 120 | 210 | 165 | 138 | 312 |
| 5 | 8.6 | A.1. + B.2.(2:1) | 15 | 2.0 | 300 | 345 | 310 | 275 | 760 |
| 6 | 8.6 | A.1. + B.2.(1:2) | 15 | 3.0 | 140 | 285 | 255 | 225 | 450 |
| 7 | 8.6 | A.1. + B.2.(2:3) | 15 | 3.0 | 150 | 288 | 225 | 183 | 480 |
| Control A.1. | 8.6 | — | 15 | 1.0 | 750 | 370 | 335 | 300 | 880 |
| Control B.2. | 8.6 | — | 15 | 5.0 | 110 | 270 | 235 | 212 | 365 |
| 8 | 6.8 | A.1. + B.2.(2:1) | 180 | 3.0 | 95 | 190 | 155 | 135 | 345 |
| 9 | 7.4 | A.1. + B.2.(1:1) | 180 | 3.0 | 140 | 190 | 150 | 130 | 355 |
| 10 | 8.5 | A.1. + B.2.(1:2) | 180 | 3.0 | 150 | 180 | 140 | 115 | 355 |

TABLE-continued

| Example | Gel pH | Mixture of Titanate Solutions (v:v) | Jabsco Pump Time (seconds) | Rate of Cross-Linking (minutes) | FANN Viscosity (centipoises) | | | | |
|---|---|---|---|---|---|---|---|---|---|
| | | | | | 0 Min. | 30 Min. | 60 Min. | 90 Min. | Maximum |
| 11 | 8.5 | A.1. + B.2.(1:3) | 180 | 4.0 | 125 | 177 | 135 | 115 | 590 |
| 12 | 9.5 | B.2. + C(1/1) | 180 | 3.0 | 210 | 305 | 220 | 160 | 440 |
| Control B.2. | 9.5 | — | 180 | 0.0 | 600 | 300 | 77 | — | 600 |
| Control C | 9.5 | — | 180 | 6.5 | 120 | 185 | 120 | 90 | 285 |
| 13 | 7.0 | A.1. + B.2.(1:1) | 180 | 4.0 | 150 | 280 | 232 | 187 | 385 |
| Control A.1. | 7.0 | — | 180 | 2.0 | 300 | 275 | 210 | 160 | 575 |
| Control B.2. | 7.0 | — | 180 | 6.75 | 120 | 242 | 195 | 160 | 345 |
| 14 | 8.5 | A.1. + B.2.(1:1) | 180 | 3.0 | 165 | 325 | 245 | 187 | 460 |
| 15 | 8.5 | A.1. + B.2.(2:1) | 180 | 2.0 | 225 | 247 | 177 | 142 | 535 |
| 16 | 7.0 | A.1. + C(3:1) | 180 | 3.5 | 150 | 260 | 198 | 158 | 375 |
| 17 | 7.0 | A.1. + C(2:1) | 180 | 5.0 | 125 | 245 | 195 | 156 | 320 |
| 18 | 7.0 | A.1. + C(1:1) | 180 | 6.5 | 115 | 220 | 175 | 140 | 282 |
| 19 | 8.5 | A.1. + C(2:1) | 180 | 3.0 | 165 | 300 | 325 | 270 | 450 |
| 20 | 8.5 | A.1. + C(1:1) | 180 | 4.0 | 135 | 260 | 202 | 157 | 380 |
| 21 | 8.5 | A.1. + C(1:2) | 180 | 6.5 | 120 | 228 | 170 | 127 | 310 |
| Control C | 8.5 | — | 180 | 8.5 | 102 | 132 | 83 | 55 | 190 |
| 22 | 7.0 | A.2. + C(2:1) | 180 | 8.5 | 120 | 217 | 180 | 150 | 262 |
| 23 | 7.0 | A.2. + C(2:1) | 180 | 9.0 | 110 | 185 | 145 | 122 | 230 |
| 24 | 7.0 | A.2. + C(1:2) | 180 | 13.0 | 110 | 160 | 125 | 102 | 190 |
| Control A.2. | 7.0 | — | 180 | 7.0 | 145 | 280 | 240 | 212 | 340 |
| Control C | 7.0 | — | 180 | 14.0 | 114 | 144 | 120 | 95 | 165 |
| 25 | 8.5 | A.2. + C(2:1) | 180 | 7.0 | 140 | 250 | 200 | 160 | 320 |
| 26 | 8.5 | A.2. + C(1:1) | 180 | 8.0 | 125 | 222 | 175 | 150 | 275 |
| 27 | 8.5 | A.2. + C(1:2) | 180 | 8.5 | 125 | 210 | 170 | 145 | 260 |
| Control A.2. | 8.5 | — | 180 | 5.5 | 170 | 275 | 230 | 190 | 350 |

We claim:

1. A composition comprising an aqueous solution containing at least two titanium compounds at least one of which effects cross-linking of hydroxyl-containing materials more rapidly than the other titanium compound, each of which titanium compounds is the reaction product of a polyol, water and an α-hydroxycarboxylic acid plus a tetravalent titanium compound of an inorganic acid, the relative amounts of the titanium compounds being such that the cross-linking rate of the solution is intermediate those of the titanium compound in the solution that has the most rapid cross-linking rate and the titanium compound in the solution having the slowest cross-linking rate, said polyol being selected from glycerol, erythritol, arabitol, xylitol, sorbitol, dulcitol, mannitol, inositol, monosaccharides, and disaccharides, and said α-hydroxycarboxylic acid being selected from lactic acid, glycolic acid, malic acid, citric acid, tartaric acid, saccharic acid, gluconic acid, glyceric acid and mandelic acid, each of said titanium compounds having an α-hydroxycarboxylic acid:titanium mol ratio between about 1:1 about 3:1, a polyol:titanium mol ratio between about 0.25:1 and about 2:1, and a water:titanium mol ratio between about 36:1 and about 60:1, and the volume:volume ratio of the titanium compound that has the most rapid cross-linking rate to the titanium compound having the slowest cross-linking rate being in the range between about 10:1 to about 1:10.

2. The composition of claim 1 wherein said volume:volume ratio is between about 3:1 and 1:3.

3. The composition of claim 2 wherein said polyol is sorbitol.

4. The composition of claim 2 wherein one of said α-hydroxycarboxylic acids is lactic acid.

5. The composition of claim 4 wherein said polyol is sorbitol, one of said acids is lactic acid, and said titanium salt is TiCl4, at a mol ratio of lactic acid:sorbitol:titanium of 1:0.5:1.

6. The composition of claim 2 wherein one of said α-hydroxycarboxylic acid is malic acid.

7. The composition of claim 6 wherein said polyol is sorbitol, one of said acids is malic acid, and said salt is TiCl4, at a malic acid:sorbitol:titanium mol ratio of 1:1:1.

8. In a hydraulic fracturing process wherein a aqueous cross-linked polysaccharide gel is introduced into a subterranean oil- or gas-contained formation at a flow rate and pressure sufficient to create or extend one or more fractures therein, the improvement comprising effecting cross-linking of the gel with the composition of claim 1.

9. The process of claim 8 further characterized in that as conditions favoring hydraulic fracturing change during the course of the process, the relative amounts of said titanium compounds are modified to compensate therefor.

10. In a hydraulic fracturing process wherein a aqueous cross-linked polysaccharide gel is introduced into a subterranean oil- or gas-containing formation at a flow rate and pressure sufficient to create or extend one or more fractures therein, the improvement comprising effecting cross-linking of the gel with the composition of claim 2.

11. The process of claim 10 further characterized in that as conditions favoring hydraulic fracturing change during the course of the process, the relative amounts of said titanium compounds are modified to compensate therefor.

12. In a hydraulic fracturing process wherein a aqueous cross-linked polysaccharide gel is introduced into a subterranean oil-or gas-containing formation at a flow rate and pressure sufficient to create or extend one or more fractures therein, the improvement comprising effecting cross-linking of the gel with the composition of claim 3.

13. The process of claim 12 further characterized in that as conditions favoring hydraulic fracturing change during the course of the process, the relative amounts of said titanium compounds are modified to compensate therefor.

14. In a hydraulic fracturing process wherein a aqueous cross-linked polysaccharide gel is introduced into a subterranean oil- or gas-containing formation at a flow rate and pressure sufficient to create or extend one or more fractures therein, the improvement comprising effecting cross-linking of the gel with the composition of claim 4.

15. The process of claim 14 further characterized in that as conditions favoring hydraulic fracturing change during the course of the process, the relative amounts of said titanium compounds are modified to compensate therefor.

16. In a hydraulic fracturing process wherein a aqueous cross-linked gel is introduced into a subterranean oil- or gas-containing formation at a flow rate and pressure sufficient to create or extend one or more fractures therein, the improvement comprising effecting cross-linking of the gel with the composition of claim 5.

17. The process of claim 16 further characterized in that as conditions favoring hydraulic fracturing change during the course of the process, the relative amounts of said titanium compounds are modified to compensate therefor.

18. In a hydraulic fracturing process wherein a aqueous cross-linked polysaccharide gel is introduced into a subterranean oil- or gas-containing formation at a flow rate and pressure sufficient to create or extend one or more fractures therein, the improvement comprising effecting cross-linking of the gel with the composition of claim 6.

19. The process of claim 18 further characterized in that as conditions favoring hydraulic fracturing change during the course of the process, the relative amounts of said titanium compounds are modified to compensate therefor.

20. In a hydraulic fracturing process wherein a aqueous cross-linked polysaccharide gel is introduced into a subterranean oil- or gas-containing formation at a flow rate and pressure sufficient to create or extend one or more fractures therein, the improvement comprising effecting cross-linking of the gel with the composition of claim 7.

21. The process of claim 20 further characterized in that as conditions favoring hydraulic fracturing change during the course of the process, the relative amounts of said titanium compounds are modified to compensate therefor.

22. In a hydraulic fracturing fluid useful in creating or extending one or more fractures in a subterranean oil- or gas-containing formation in which the fluid contains water, a cross-linking polysaccharide polymer, a proppant and a cross-linking agent, the improvement wherein the cross-linking agent is the composition of claim 1.

23. In a hydraulic fracturing fluid useful in creating or extending one or more fractures in a subterranean oil- or gas-containing formation in which the fluid contains water, a cross-linking polyumer, a proppant and a cross-linking agent, the improvement wherein said cross-linking agent is the compensation of claim 2.

24. In a hydraulic fracturing fluid useful in creating or extending one or more fractures in a subterranean oil- or gas-containing formation in which the fluid contains water, a cross-linking polymer, a proppant and a cross-linking agent, the improvement wherein said cross-linking agent is the composition of claim 3.

25. In a hydraulic fracturing fluid useful in creating or extending one or more fractures in a subterranean oil- or gas-containing formation in which the fluid contains water, a cross-linking polymer, a proppant and a cross-linking agent, the improvement wherein said cross-linking agent is the composition of claim 4.

26. In a hydraulic fracturing fluid useful in creating or extending one or more fractures in a subterranean oil- or gas-containing formation in which the fluid contains water, a cross-linking polymer, a proppant and a cross-linking agent, the improvement wherein said cross-linking agent is the composition of claim 5.

27. In a hydraulic fracturing fluid useful in creating or extending one or more fractures in a subterranean oil- or gas-containing formation in which the fluid contains water, a cross-linking polymer, a proppant and a cross-linking agent, the improvement wherein said cross-linking agent is the composition of claim 6.

28. In a hydraulic fracturing fluid useful in creating or extending one or more fractures in a subterranean oil- or gas-containing formation in which the fluid contains water, a cross-linking polymer, a proppant and a cross-linking agent, the improvement wherein said cross-linking agent is the composition of claim 7.

* * * * *